United States Patent
Andelin et al.

[19]

[11] Patent Number: 6,110,128
[45] Date of Patent: Aug. 29, 2000

[54] BONE MARROW BIOPSY NEEDLE AND METHOD FOR USING THE SAME

[76] Inventors: John B. Andelin, 4940 140 Ave., NW., Lot 62, Williston, N. Dak. 58801-8605; Martin T. White, 5231 S. Misty View La., Taylorsville, Utah 84123

[21] Appl. No.: 09/210,053

[22] Filed: Dec. 11, 1998

[51] Int. Cl.[7] .................................................... A61B 5/00
[52] U.S. Cl. ............................................................. 600/566
[58] Field of Search ............................ 600/562, 564–567, 600/570, 571

[56] References Cited

U.S. PATENT DOCUMENTS

| | | | |
|---|---|---|---|
| 4,366,822 | 1/1983 | Altshuler | 600/566 |
| 4,469,109 | 9/1984 | Mehl | 600/566 |
| 4,543,966 | 10/1985 | Islam et al. | |
| 4,649,918 | 3/1987 | Pegg et al. | |
| 4,903,709 | 2/1990 | Skinner | |
| 5,064,411 | 11/1991 | Gordon | 600/567 |
| 5,538,008 | 7/1996 | Crowe | 600/564 |
| 5,885,226 | 3/1999 | Rubinstein et al. | 600/564 |

FOREIGN PATENT DOCUMENTS

| | | | |
|---|---|---|---|
| 001602487 | 10/1990 | U.S.S.R. | 600/564 |

*Primary Examiner*—Max Hindenburg
*Attorney, Agent, or Firm*—Harry M. Weiss; Jeffrey Weiss; Harry M. Weiss & Associates, P.C.

[57] ABSTRACT

A biopsy needle assembly that is an improvement over the Jamshidi biopsy needle assembly is provided. The improved biopsy needle assembly includes a cannula with a uniform diameter internal surface defining an inner biopsy tissue sample receiving and retaining bore having projections thereon, and a stylet having rounded edges with at least one V-shaped groove at a distal cutting tip removably received within the bore of the cannula. The projections may be barbs, annular or spiral ribs that line the inner biopsy tissue sample receiving and retaining bore. The stylet may include a quick release knob for engaging with an improved coupling at the proximal end of the cannula. The improved coupling is substantially cylindrical with a cross handle substantially in the middle thereof. The coupling may also include internal threads engaging a syringe. The improved biopsy needle assembly permits more consistent acquisition of an adequate tissue sample for biopsy and is less painful to the patient.

17 Claims, 3 Drawing Sheets

BONE MARROW BIOPSY NEEDLE AND METHOD FOR USING THE SAME

FIELD OF THE INVENTION

This invention relates generally to a medical instrument and more particularly to an improved bone marrow biopsy needle and method for using the same.

BACKGROUND OF THE INVENTION

The analysis of bone marrow is an invaluable tool for diagnosing a variety of hematologic and nonhematologic disease processes. Bone marrow is the soft material that fills the cavities of the bones. A bone marrow biopsy is performed to obtain a bone marrow sample for analysis. The bone marrow biopsy is a common, relatively simple procedure. Generally, the biopsy procedure is performed under local anesthesia, with the bone marrow sample obtained from the posterior superior iliac spine. In order to be diagnostically useful, the sample should be of adequate size with little or no distortion of structure. Moreover, a marrow sample should be easily obtained with minimal discomfort or risk to the patient. More specifically, following adequate local anesthesia of the periosteum, the biopsy needle with the stylet locked in place is advanced into the bone cortex and cavity (posterior iliac crest). Once the cortex of the bone is penetrated, the stylet is then removed. The aspirate (fluid from the marrow cavity) is drawn into a syringe and slides are quickly made from the aspirate. The biopsy needle is then slowly and gently advanced with smooth clockwise-counterclockwise motions until an adequate bone marrow sample is obtained. The biopsy needle is then rotated completely several times along its long axis and slowly removed with alternating rotary motions. This is done to break the sample off from the bone so that when the needle is withdrawn, the sample is retained in the bore of the needle. Once the needle is withdrawn, the bone marrow sample is gently removed with a long probe introduced through the distal cutting tip of the biopsy needle. The bone marrow sample can be expelled through the proximal portion of the biopsy needle and then appropriately analyzed.

In recognition of biopsy requirements, many instruments have been devised in order to sample bone marrow. Unfortunately, most of them do not consistently obtain an adequate sample with little or no distortion of structure. The Jamshidi biopsy needle device (Jamshidi and Swaim, J. Lab. Clin. Med., February 1971), for example, has been widely used but suffers from several deficiencies. That biopsy needle device generally includes a generally cylindrical cannula with a tapered distal portion including a sharp cutting Lip. The interior diameter of the distal portion is also tapered radially toward the cutting tip. A proximal end includes a coupling including a pair of finger grips, the coupling threadably engaging with a cap that locks over a knob of a stylet designed to interlock to fit the core. The stylet projects approximately 1 to 2 mm. beyond the cutting tip to protect a cutting edge and provide a means of entering the marrow. The Jamshidi device also accommodates a syringe with a catheter (tapered) tip. Unfortunately, a substantial portion of the sample may be lost during removal of the Jamshidi biopsy needle because the sample slides out of the needle necessitating repeated attempts to obtain an adequate sample. Moreover, the discovery of and loss of the tissue sample after enduring the rather painful procedure is disturbing to most patients. Furthermore, it is frustrating for the doctor to "complete" the procedure only to find the tissue sample lost after removal of the needle from the patient's body. In addition, the use of the Jamshidi needle (and other similar designs) require extensive rotary motion to be employed in an attempt to break the tissue sample off from the bone so it will be retained in the bore of the needle. This maneuver causes substantial and unnecessary pain and anxiety to patients.

Accordingly, there has been a need for a novel improved bone marrow biopsy needle that substantially prevents the loss of bone marrow sample and the method for using the same. There is a further need for a novel improved bone marrow biopsy needle and method that consistently obtain an adequate sample. There is a still further need for a novel improved bone marrow biopsy needle and method that permit obtaining a sample with little or no distortion of structure. There is an additional need for a novel improved bone marrow biopsy needle and method that allow bone marrow to be easily obtained, with minimal discomfort or risk to the patient. There is also a need for a novel improved bone marrow biopsy needle that will engage with a wide range of syringe types. The present invention fulfills these needs and provides other related advantages.

SUMMARY OF THE INVENTION

In accordance with this invention, it is an object of this invention to provide an improved bone marrow biopsy needle and method for using the same that substantially prevent the loss of bone marrow sample and the method for using the same.

It is another object of this invention to provide an improved bone marrow biopsy needle and method that consistently obtain an adequate sample.

It is a further object of this invention to provide an improved bone marrow biopsy needle and method that permit obtaining a sample with little or no distortion of structure.

It is a still further object of this invention to provide an improved bone marrow biopsy needle and method that allow bone marrow to be easily obtained, with minimal discomfort or risk to the patient.

It is yet another object of this invention to provide an improved bone marrow biopsy needle and method that can engage with a wide variety of syringe types. The present invention resides in an improved biopsy needle assembly that retains a substantial portion of the extracted tissue, that causes little or no alteration of the tissue, and that allows bone marrow to be easily obtained. The present invention substantially assures that an adequate sample is obtained with the avoidance of repeated attempts and simplifies the biopsy procedure thus decreasing patient discomfort. The improved bone marrow biopsy needle assembly comprises, generally, a cannula with an internal surface with projections thereon and defining an inner biopsy tissue sample receiving and retaining bore of substantially constant internal diameter, and a stylet having rounded edges removably received within the inner biopsy tissue sample receiving and retaining bore. An improved coupling at a proximal end of the cannula engages with the stylet or with a syringe.

The cannula has a uniform, external elongated cylindrical configuration. The cannula includes a uniform diameter distal cutting end and the proximal end with the coupling. An external surface of the cannula may be marked with gradations beginning from the distal cutting end.

In a preferred embodiment, the improved coupling may be substantially cylindrical with a cross handle substantially in the middle thereof. A distal end of the coupling narrows for a close fit around the cannula. The proximal end of the coupling includes a pair of spaced apart outwardly-extending opposed dowels or threads on the outside thereof and threads on the inside thereof.

The inner biopsy receiving and retaining bore is preferably of substantially constant internal diameter, approximately 3 mm. The bore extends axially substantially the length of the cannula. The internal surface may include projections that line the bore. The projections include barbs, annular ribs, or spiral ribs. The projections project backward from a distal cutting end of the cannula. The projections are spaced at short intervals along the internal surface of the cannula around substantially the internal circumference, in a regular pattern or more randomly. The projections preferably begin just inside the distal end of the cannula and preferably extend about one inch into the cannula. The projections preferably are positioned at an angle from about 1 degree to about 90 degrees, preferably no greater than approximately a 45-degree angle to the internal surface of the cannula. The internal surface of the cannula may alternatively be roughened by etching with cross-hatches, spackling, grooves, or altered by similar friction-enhancing processes designed to facilitate the retention of the bone marrow sample in the bore of the biopsy needle.

The stylet is elongated with a distal end projecting slightly beyond the distal cutting end of the cannula when fully engaged. The rounded edges of the stylet prevent the stylet from getting hung up on the projections when the stylet is placed in and removed from the inner biopsy tissue receiving and retaining bore. The tip of the stylet bears one or more V-shaped grooves with sharp edges. The purpose of these grooves is to provide a cutting edge to the stylet as the biopsy needle is rotated through the cortex of the bone. A conventional probe may be provided for removal of the tissue sample from the bore.

In a preferred embodiment, the stylet includes an integral cap at a proximal end. The cap is substantially cylindrical with a reduced diameter distal portion. The distal portion of the integral cap includes a pair of opposed L-shaped tracks for twist-fit engagement with the pair of outwardly-extending spaced apart opposed dowels on the proximal end of the coupling. The cap may be spring loaded to provide tension during locking into the cannula. As the dowels travel clockwise, the spring-loaded cap provides the required tension to lock the stylet in place during cutting. After cutting, the cap is pressed forward to release tension and removed counterclockwise from the cannula.

A syringe with either a conventional tapered tip configuration or a LUER LOCK configuration may engage in the improved coupling. The tapered tip syringe is held in the proximal end of the improved coupling by friction fit. The LUER LOCK syringe is held there by threadable engagement.

A method of using the improved biopsy needle assembly is also provided.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
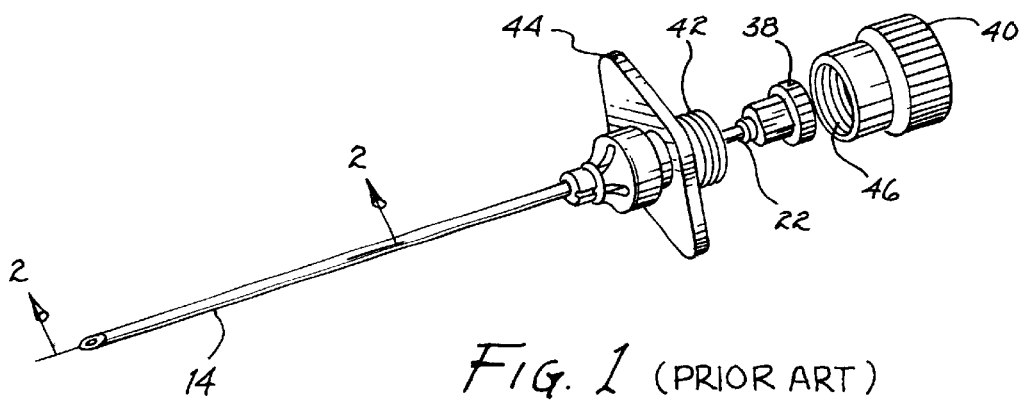
FIG. 1 is a perspective assembly view of a Jamshidi biopsy needle assembly, illustrating a cap that threadably engages with a conventional coupling at the proximal end of a cannula over a screw-type knob of a conventional stylet that is received in the cannula.
Figure 2:
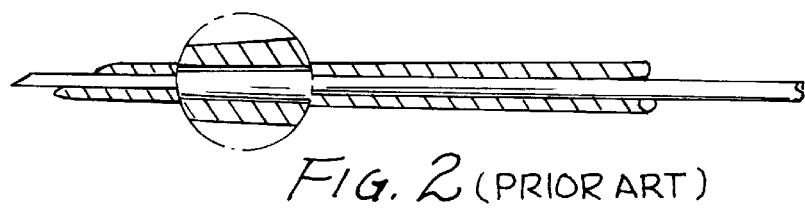
FIG. 2 is an enlarged sectional view of the cannula of the Jamshidi biopsy needle assembly taken generally along the line 2—2 of FIG. 1 with a tapered distal portion thereof shown in the enlarged encircled portion and illustrating the stylet fully received within a bore of the cannula.

As shown in the drawings for purposes of illustration, the present invention is concerned with an improved bone marrow biopsy needle assembly, generally designated in the accompanying drawings by the reference number 10 and the method for using the same. The improved biopsy needle assembly 10 comprises, generally, a biopsy needle 12 including a cannula 14 with an internal surface 16 defining an inner biopsy tissue sample receiving and retaining bore 18 having a series of projections 20, and an elongated stylet 22 having rounded side edges removably received within the bore 18 of the cannula 14. An improved coupling 24 at the proximal end of the cannula 14 may be releasably engaged with the stylet 22 or with a syringe 26.

The cannula 14 has a uniform, external elongated cylindrical configuration. The exterior surface beginning at the distal end of the cannula 14 may be marked with gradations 28, typically in cm or mm increments to assist physicians in determining the depth of penetration during insertion and removal of the biopsy needle. The gradations 28 may be etched into the cannula 14 or made in any other conventional manner.

Figures 4, 5:
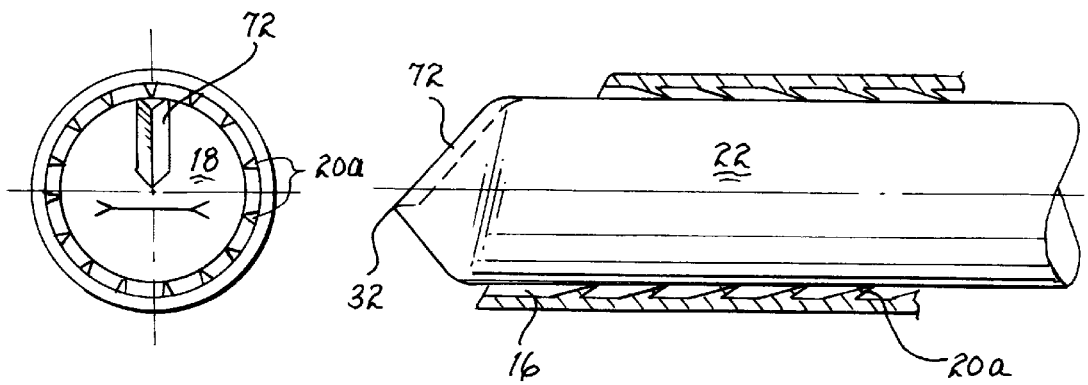
FIG. 4 is an enlarged sectional view of an improved bone marrow biopsy needle embodying the invention including a distal cutting end portion of a cannula and a stylet having rounded side edges and a v-shaped groove at the cutting tip thereof within an inner biopsy tissue receiving and retaining bore, the bore having barbs therein.
FIG. 5 is a cross-sectional view of the improved bone marrow biopsy needle, illustrating the provision of the barbs lining the inner biopsy tissue receiving and retaining bore.
Figure 6:
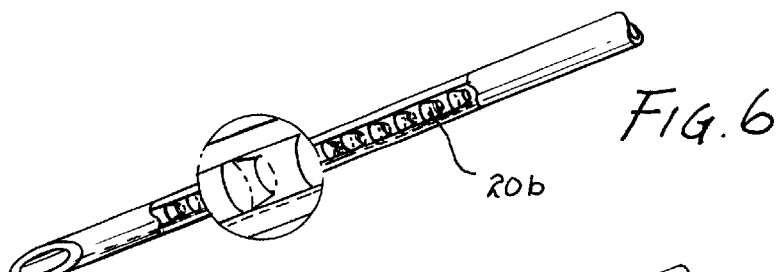
FIG. 6 is a perspective view of a portion of the cannula with the outer surface cut away revealing annular ribs lining the inner biopsy receiving and retaining bore of the cannula, an enlarged encircled region showing the annular ribs in more detail.
Figure 7:
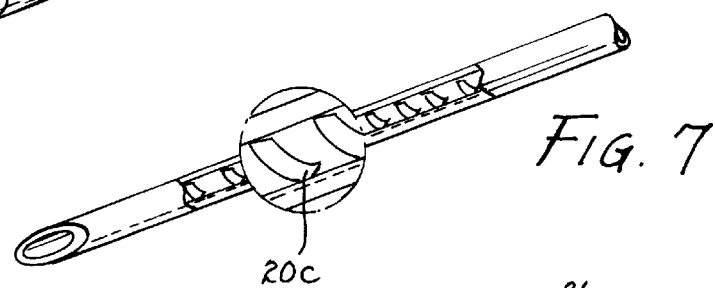
FIG. 7 is a perspective view of a portion of the cannula with the outer surface cut away revealing spiral ribs in a spiraling pattern along the inner biopsy receiving and retaining bore of the cannula, an enlarged encircled region showing the spiraling ribs in more detail.
Figure 9:
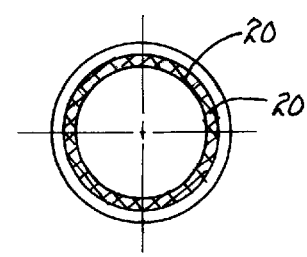
FIG. 9 is a cross-sectional view of the improved bone marrow biopsy needle illustrating the provision of projections lining the inner biopsy tissue receiving and retaining bore.

The inner biopsy receiving and retaining bore 18 is of substantially constant internal diameter, approximately 3 mm. The bore 18 extends axially substantially the length of the cannula 14. The projections 20a, 20b, and 20c that line the bore 18 provide substantial gripping action when withdrawing the biopsy needle 12 to prevent the tissue sample (not shown) from sliding out of the needle when the needle is removed from the patient. The projections 20 are spaced at short intervals along the internal surface 16 of the bore 18 as illustrated in FIGS. 5 and 9 around substantially the internal circumference of the cannula 14. The projections 20a–c preferably begin just inside the distal end 30 of the cannula 14 and preferably extend into about one inch of the cannula. It is to be appreciated, however, that the projections 20a–c may extend substantially the length of the cannula 14 or less than about the two-thirds. The projections 20 are relatively short so as not to disrupt or distort the tissue sample, and are positioned from about 1 degree to about 90 degrees, preferably no greater than a 45 degree angle to the internal surface of the cannula 14. The projections 20 are preferably integrally formed with the cannula 14 such as by cuts into the molten metal, preferably stainless steel, forming the cannula. Of course, the projections 20 may be made in other manners and with other medical grade materials depending on the manufacturing processes that are used. For example, the projections 20 may be machined by back-reaming or other means necessary to achieve projections in a backward acute angle. The projections may be in the form of barbs 20a that project backward from a distal end 30 of the cannula 14 as illustrated in FIG. 4. The projections 20 may also be continuous annular ribs 20b as illustrated in FIG. 6 that are spaced about one to about two mm apart, although other spacing may be envisioned. The projections 20 may also be spiral ribs 20c as illustrated in FIG. 7 that run uniformly in a spiral fashion along the inner circumference of the cannula 14.

Figure 13:
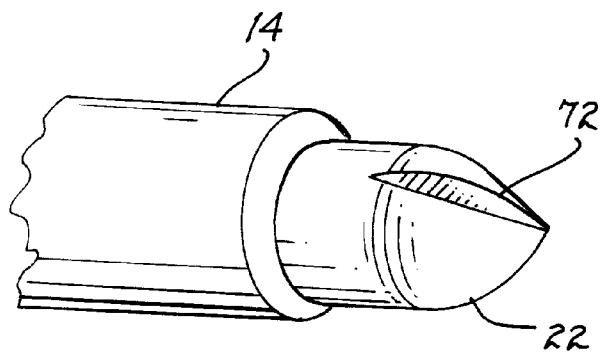
FIG. 13 is a perspective view of the distal tip of the biopsy needle with the stylet tip protruding therefrom, the stylet including the V-shaped groove therein.

As illustrated in FIG. 4, a cutting distal end 32 of the stylet 22 projects slightly beyond the biopsy needle 12 to prevent soft tissue from entering the needle before the needle penetrates the bone. The rounded side edges of the stylet 22 prevent the stylet 22 from getting hung up on the projections 20 when the stylet 22 is placed in and removed from the bore 18. As illustrated in FIG. 13, one or more V-shaped grooves 72 with sharp edges are made in the distal tip of the stylet, by cutting or otherwise. This facilitates cutting through the cortex of the bone as the biopsy device is advanced into the marrow by rotary motions.

Figure 8:
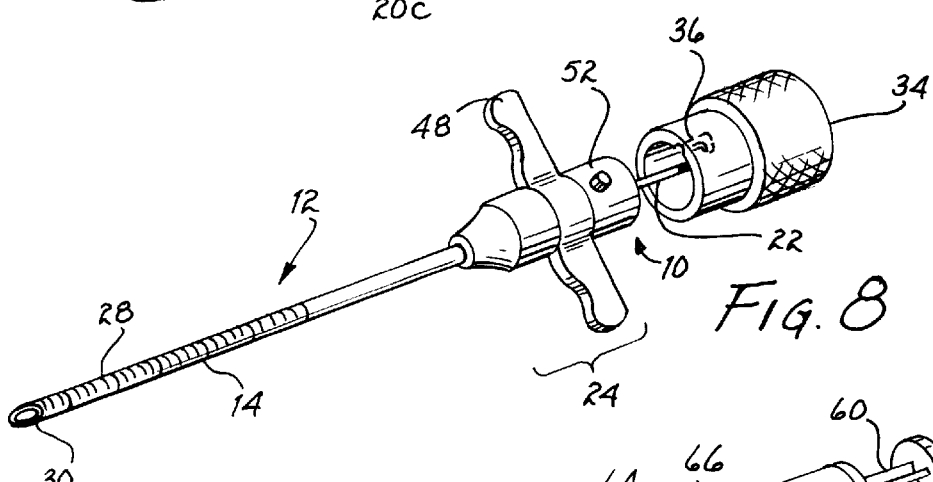
FIG. 8 is a perspective assembly view of the improved biopsy needle assembly including the cannula having gradations marked on a exterior surface at a distal end thereof and an improved coupling at a proximal end thereof for releasably coupling with a cap of the stylet, the coupling including a pair of outwardly extending opposed dowels for engagement in a pair of L-shaped tracks of the cap.

In a preferred embodiment as illustrated in FIG. 8, the stylet 22 may include an integral cap 34 at a proximal end thereof. The inside of the cap includes a spring (not shown) or O-ring (not shown) to provide tension during locking. The proximal end of the cap is knurled for better gripping action while the diameter of the distal end of the cap may be reduced and includes a pair of L-shaped tracks 36, the purpose for which will be hereinafter described.

The stylet 22 of the preferred embodiment is adapted to be releasably engaged with the improved coupling 24. The improved coupling 24 is substantially cylindrical with a cross handle 48 substantially in the middle thereof for better gripping action. A distal end 50 of the coupling 24 narrows to the outside diameter of the cannula 14 and the proximal end 52 of the coupling includes a pair of outwardly-extending spaced apart opposed dowels 54 for twist fit reception in the pair of L-shaped tracks 36 of the integral cap. The coupling has an axial bore (not shown) therethrough for slide through reception of the elongated portion of the stylet 22 and aspirate passage when engaging the syringe.

The improved coupling also engages with a conventional tapered tip syringe 26a (FIG. 12) or a LUER LOCK syringe 26b (FIGS. 10 and 11)(Sherwood Medical, St. Louis, Missouri). The conventional tapered tip and the LUER LOCK syringes are fitted with a piston 60 for drawing in aspirate. A tip 62 of both types of syringes 26a and 26b narrows into an aperture 64. The LUER LOCK syringe 26b includes an additional upstanding wall 66 concentrically surrounding the narrow tip 62. The LUER LOCK upstanding wall 66 includes a series of threads 68 on an interior surface, the purpose for which will be hereinafter described.

Figure 10:
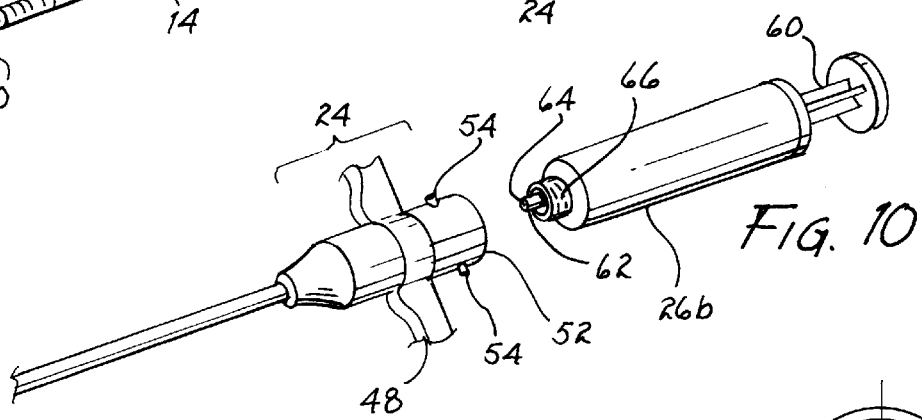
FIG. 10 is a perspective assembly view of a portion of the cannula, illustrating the coupling releasably engaging with a LUER LOCK syringe.
Figure 11:
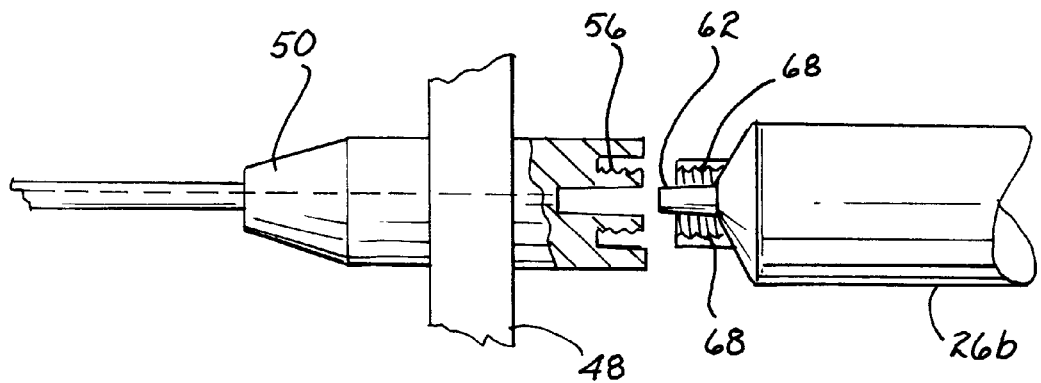
FIG. 11 is a sectional view of the coupling and the Luer Lock syringe, illustrating the manner in which the coupling threadably engages with the LUER LOCK syringe.
Figure 12:
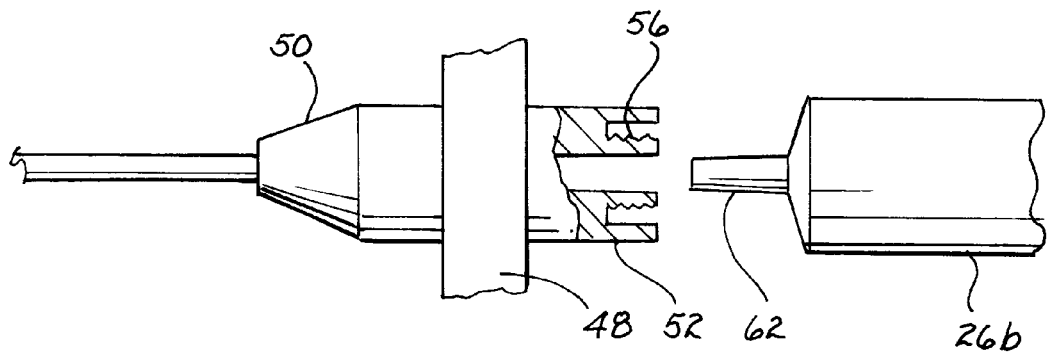
FIG. 12 is a sectional view of the coupling and the tapered tip syringe, illustrating the manner in which the tapered tip syringe is received and maintained in the coupling by friction fit.

The improved coupling 24 includes threads 56 on the inside thereof. Referring to FIG. 12, the tip 62 of the tapered tip syringe 26a is engaged in the improved coupling 24 by friction fit. Referring to FIGS. 10 and 11, the inside threads 56 at the proximal end of the improved coupling 24 threadably engages with the threads 68 on the upstanding wall 66 of the LUER LOCK syringe 26b.

It is to be appreciated that the improved biopsy needle assembly may be fitted with the conventional coupling and stylet shown in FIG. 1 rather than with the improved coupling and stylet of the preferred embodiment. The conventional stylet includes a screw type knob 38 at a proximal end. A cap 40 having internal threads 46 threadably engages with a threaded proximal end 42 of the conventional coupling over the screw type knob 38. The conventional coupling includes a pair of finger grips 44.

Figure 3:
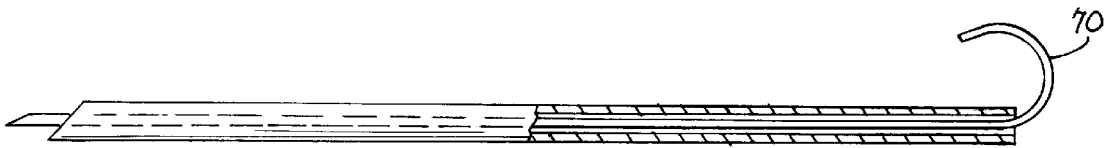
FIG. 3 is a sectional view of the bore of the cannula of FIG. 1 with a probe therein.

In the method of the invention, the stylet 22 is removed from the cannula 14 once the desired location within a patient is reached. The tissue sample is then drawn into the bore 18 and removed therefrom by, for example, a conventional probe 70 as illustrated in FIG. 3.

From the foregoing, it is to be appreciated that the bone marrow biopsy procedure using the improved biopsy needle assembly 10 of the present invention is simpler, quicker, less painful with fewer attempts required, and from which an adequate tissue sample is consistently obtained. Although a particular embodiment of the invention has been described in detail for purposes of illustration, various modifications may be made without departing from the spirit and scope of the invention. Accordingly, the invention is not to be limited, except as by the appended claims.

I claim:

1. A biopsy needle assembly comprising, in combination:
   a cannula defining an inner biopsy tissue sample and receiving bore of substantially constant internal diameter
   spiral ribs running uniformly along an interior surface of said bore; and
   an elongated stylet having rounded side edges removably received within the inner biopsy tissue sample receiving and retaining bore of the cannula.

2. The biopsy needle assembly of claim 1, wherein the cannula comprises a hollow, elongated cannula with a uniform, external cylindrical configuration.

3. The biopsy needle assembly of claim 1, wherein the elongated stylet has a distal cutting tip with at least one V-shaped groove therein.

4. The biopsy needle assembly of claim 1, wherein the spiral ribs extend about one inch into the cannula from a distal end thereof.

5. The biopsy needle assembly of claim 1, wherein the spiral ribs project backward from a distal end of the cannula.

6. The biopsy needle assembly of claim 1, wherein the spiral ribs are positioned at an angle of from about one degree to about 90 degrees.

7. The biopsy needle assembly of claim 6, wherein the spiral ribs are positioned at an angle no greater than approximately a 45 degree angle to an internal surface of the cannula.

8. The biopsy needle assembly of claim 1, wherein a proximal end of the cannula includes a coupling having a bore therethrough.

9. The biopsy needle assembly of claim 8, wherein the bore receives the elongated stylet.

10. The biopsy needle assembly of claim 8, wherein the coupling includes a pair of outwardly-extending opposed dowels to engage in a pair of L-shaped tracks in a knob of the elongated stylet.

11. The biopsy needle assembly of claim 10, wherein the knob of the stylet includes a spring for twist fit engagement.

12. The biopsy needle assembly of claim 8, wherein the coupling engages one of a LUER LOCK or a tapered tip syringe.

13. The biopsy needle assembly of claim 12, wherein the coupling includes internal threads for engaging the LUER LOCK syringe.

14. The biopsy needle assembly of claim 1, wherein an outer surface of the distal end of the cannula is marked with gradations.

15. A biopsy needle assembly comprising in combination:

a hollow elongated cannula with a substantially uniform external configuration and having an internal surface with spiral ribs running uniformly thereon and defining an inner biopsy tissue sample receiving and retaining axial bore of substantially constant internal diameter; and a coupling of the proximal end of the cannula for engaging with one of a stylet or a syringe, the coupling being substantially cylindrical with a cross handle substantially in the middle thereof and including at a proximal end thereof a pair outwardly-extending spaced apart opposed dowels on an external surface for engaging the stylet and internal threads on an internal surface for engaging the syringe.

16. The biopsy needle assembly of claim 15, wherein the stylet has a distal cutting tip with at least one V-shaped groove therein.

17. A method of obtaining a tissue sample from the body of a patient, comprising the steps of:

providing a biopsy needle assembly including a hollow cannula having an internal surface with spiral ribs running uniformly thereon and defining an inner tissue sample and retaining bore of substantially constant internal diameter and an elongated stylet having rounded side edges and received within the bore of the cannula in a fully inserted position;

inserting the biopsy needle assembly into the patient using a cutting distal end of the stylet to penetrate the skin of the patient;

removing the stylet from within the inner tissue sample receiving and retaining bore of the cannula;

drawing the tissue sample into the inner tissue sample receiving and retaining bore; and extracting the tissue sample from the inner tissue sample receiving and retaining bore.

* * * * *